United States Patent [19]

Olin

[11] 4,255,342
[45] Mar. 10, 1981

[54] SYNTHESIS OF PHENOXYANTHRAQUINONES

[75] Inventor: Arthur D. Olin, Lakewood, N.J.

[73] Assignee: Toms River Chemical Corporation, Toms River, N.J.

[21] Appl. No.: 25,523

[22] Filed: Apr. 2, 1979

[51] Int. Cl.$^3$ ............................................. C07C 50/34
[52] U.S. Cl. ................................................... 260/383
[58] Field of Search ........................................ 260/383

[56] References Cited

U.S. PATENT DOCUMENTS 3,399,952  9/1968  Hosoda ............................... 260/383

FOREIGN PATENT DOCUMENTS 2228334  1/1974  Fed. Rep. of Germany .
53-37650  6/1978  Japan .

Primary Examiner—Patrick Garvin
Assistant Examiner—Raymond K. Covington
Attorney, Agent, or Firm—Edward McC. Roberts

[57] ABSTRACT

A method of synthesizing phenoxyanthraquinones in the absence of excess phenol, water-miscible alcohols or polar aprotic solvents. Phenoxyanthraquinones are synthesized in high yield and purity by treatment of the corresponding chloro- or nitroanthraquinone with an equivalent of alkali metal phenoxide, particularly potassium phenoxide in a liquid aromatic solvent which is a chloro-substituted benzene, a lower alkyl-substituted benzene, or a loweralkyl-chloro-substituted benzene. The use of the inventive solvents results in high yields of readily isolable, substantially pure product. The used solvent is readily recoverable without the pollution potential of excess phenol or difficultly recoverable water-miscible solvents.

13 Claims, No Drawings

SYNTHESIS OF PHENOXYANTHRAQUINONES

BACKGROUND OF THE INVENTION

Phenoxyanthraquinones are useful as intermediates for the production of dyes as well as other dye intermediates. In the dye industry, phenoxyanthraquinones are usually synthesized by the reaction of a nitro- or haloanthraquinone with caustic in the presence of excess phenol as both the reactant and solvent.

In the work-up for such processes the phenol melt is diluted with water, the phenoxyanthraquinone is filtered off, and the excess phenol remains in the filtrate and wash. Because of the difficulty in the recovery of the phenol, this process is both expensive and ecologically undesirable. Furthermore, an alkaline reslurry of the product is often needed in order to completely free the product from unreacted excess phenol, and there are substantial yield losses.

This problem has been recently addressed in German OLS No. 2,228,334, in which a water-miscible polar aprotic solvent such as dimethyl formamide, dimethyl sulfoxide, or N-methyl pyrrolidone is used with only a small excess of the phenol and caustic, reacting with the α-nitro-anthraquinone substrate. In this case the excess phenol is being replaced by an unrecovered and relatively expensive solvent. Recovery of water-miscible, polar, aprotic solvents from an aqueous medium is prohibitively difficult and expensive in terms of time, equipment and energy.

In the art, the treatment of chloro- or nitroanthraquinones with phenol and caustic or with alkali phenoxide to produce phenoxyanthraquinones has only been carried out in the presence of polar solvents such as phenol, alcohol, dimethyl formamide, dimethyl sulfoxide or N-methylpyrrolidone.

An object of this invention is to manufacture phenoxyanthraquinones from chloro- or nitroanthraquinone and alkali phenoxide in high yields of readily-isolable product, without the use of excess phenol, water-miscible alkanols or water-miscible polar aprotic solvents.

A further object of this invention is the substitution, for the solvents of the art, of water-insoluble, non-polar, non-protic solvents which are cheap and readily recoverable from water.

THE INVENTION

The objects of this invention have been realized by treating a chloro- or nitroanthraquinone with a substantial equivalent of an alkali phenoxide, particularly potassium phenoxide, in an aromatic solvent such as a chloro-, lower alkyl-, or loweralkyl-chloro-benzene. The eligible solvents are liquid, aromatic, non-polar, non-protic solvents. The eligible solvents are exemplified by chlorobenzene, o-xylene, o-dichlorobenzene and o-chlorotoluene. Particularly useful are o-xylene and o-chlorotoluene, with the latter being preferred.

According to this invention, stoichiometric amounts of caustic, such as lithium hydroxide, sodium hydroxide or the preferred potassium hydroxide, and phenol are heated at reflux in the selected aromatic solvent, with azeotropic removal of the water formed during the reaction. When all of the water of reaction has been removed by azeotropic distillation, i.e. the formation of alkali phenoxide is complete, the chloroanthraquinone or nitroanthraquinone is introduced into the reaction vessel, and is allowed to react for a few hours at a temperature in the range of 90° to 150° C. It is possible to add the chloro- or nitroanthraquinone to the reaction vessel before the formation of the alkali phenoxide is complete, but this sometimes leads to lowered yields.

The resulting phenoxyanthraquinones are easily isolated by steam distillation of the aromatic solvent followed by filtration and washing of the product. After drying, the desired compounds are readily obtained generally in greater than 90% of theoretical yield. Thus, the process of this invention provides a high space-time yield at lower costs than the art processes. The invention process further advantageously results in a water effluent from the work-up which is substantially uncontaminated with excess phenol and solvent. The recovered aromatic reaction solvent from the steam distillation can be readily separated from the water, dried and re-used.

When the selected starting anthraquinone is α-nitroanthraquinone, a reaction temperature of 90° to 120° C. is sufficient, while α-chloroanthraquinone requires higher temperatures in the range of 120° to 150° C. This difference in reactivity between α-nitro and αchloro groups can be taken advantage of to make an α-chloro-phenoxyanthraquinone by the selective replacement of the α-nitro group in a nitro-chloroanthraquinone such as 1-chloro-5-nitroanthraquinone, at a reaction temperature in the range of 90° to 110° C.

When the selected starting anthraquinone is di-substituted at two of the 1-, 4-, 5- and 8-positions, with two chloro-groups, two nitro-groups, or one of each, a double replacement may be effected to produce the corresponding diphenoxyanthraquinone, by use of two equivaents of alkali phenoxide.

The general reaction may be represented as follows:

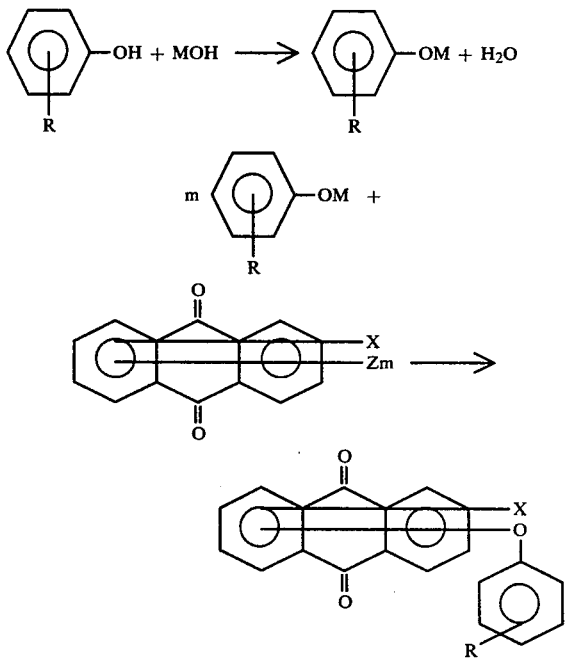

Where R is hydrogen, lower alkyl or lower alkoxy,
X is hydrogen, methyl or chloro
Z is chloro or nitro at the 1-, 4-, 5- or 8-position, provided that Z is nitro when X is chloro,
M is alkali metal, and m is 1 or 2.

The inventive solvent is used in both steps of the above reaction and serves to remove the water from the first step, azeotropically.

As alkali hydroxide, MOH, both sodium hydroxide and potassium hydroxide work nicely, but potassium hydroxide is preferred. A substantially stoichiometric amount of alkali hydroxide, with no more than about 5% excess, is preferred.

Wet solvents and wet phenols may be used, but, in such case, best results are obtained if this moisture as well as the water of reaction are removed azeotropically during and by the end of the first step.

In most cases a solvent charge of about 2 to 4 parts per part of anthraquinone starting material is adequate. With special stirring equipment, such as a heavy duty Venuleth reactor, 1 to 2 parts of solvent is sufficient.

The invention is more specifically set out in the following Examples.

EXAMPLE 1

1-Chloro-5-Phenoxyanthraquinone

A mixture of 10.3 g. phenol, 6.5 g. potassium hydroxide and 260 g. o-chlorotoluene was stirred and heated at reflux, and the water-containing azeotrope was removed by distillation. Initially, the azeotrope came over at 94° C., and the reaction mixture was heated until the water-freed solvent distilled over at a head temperature of ca. 156° C. The reaction slurry was cooled to 100° C., and 28.8 g. of 1-chloro-5-nitroanthraquinone was added over ½ hour at 100° to 105° C. The reaction mixture was held for 6 hours at 100° to 105° C. and then drowned into 500 g. water and steam distilled to remove the solvent. After filtering the hot aqueous slurry the product was dried in the vacuum oven at 60°-70° C. A 31.4 g. (93.9% of theory) yield of 1-chloro-5-phenoxyanthraquinone was obtained.

| Analysis: | % Found | % Theory |
|---|---|---|
| Chlorine | 10.2 | 10.6 |
| Nitrogen | 0.3 | 0 |

A thin layer chromatogram showed the absence of starting material.

EXAMPLE 2

1,5- and 1,8-Diphenoxyanthraquinone from Mixed 1,5- and 1,8-Dinitroanthraquinone A mixture of 56.4 g. phenol, 38.2 g. potassium hydroxide and 349 g. of o-chlorotoluene was stirred and heated and the water removed by azeotropic distillation to give a slurry of the potassium phenoxide in the dried aromatic solvent. The reaction mixture was cooled to 100° to 105° C. and 86.5 g. of a 1,5-, 1,8-dinitroanthraquinone mixture added in 55 minutes. The reaction mixture was held at 100° to 105° C. for 3 hours, steam-distilled free of solvent and the product recovered by filtration and drying. A 106.6 g. yield (94.9% of theory) of a mixture of 1,5-, 1,8-diphenoxyanthraquinone was obtained.

Analysis for residual nitrogen: 0.2%.

A thin layer chromatogram showed the absence of starting material.

EXAMPLE 3

1,5- and 1,8-Di-t-butylphenoxyanthraquinone from Mixed 1,5- and 1,8-Dinitroanthraquinone A mixture of 90.1 g. of t-butylphenol and 38.2 g. potassium hydroxide, in 500 g. o-chlorotoluene, was converted to potassium t-butylphenoxide by azeotropic distillation to remove the water of reaction and 86.5 g. of a mixture of 1,5- and 1,8-dinitroanthraquinone were added at 100° to 105° C. The whole was stirred 3 hours at 100° to 105° C. and the product isolated and dried after steam distillation of the solvent. The yield was 146.3 g. (96.7% of theory) of a yellow solid.

Analysis for residual nitrogen: 0.2%.

A thin layer chromatogram showed the absence of starting material.

EXAMPLE 4

1,8-Diphenoxyanthraquinone from 1,8-Chloronitroanthraquinone

A mixture of 21 g. phenol, 13 g. potassium hydroxide and 270 g. o-chlorotoluene was converted to a water-free slurry of potassium phenoxide by azeotropic distillation of all the water formed. After cooling back to 100° C., 28.8 g. of 1-chloro-8-nitroanthraquinone was charged and the whole heated and stirred at 130° C. for 6 hours. The product was isolated by steam distillation, filtration, washing and drying. A 37.7 g. yield (96.2% of theory) of a product identical to authentic 1,8-diphenoxyanthraquinone in a thin layer chromatogram and free of starting material was obtained.

Analysis for residual chlorine: 1.1%.

EXAMPLE 5

1,5- and 1,8-Diphenoxyanthraquinone from Mixed 1,5- and 1,8-Dichloroanthraquinone A mixture of 120 g. phenol, 79.5 g. potassium hydroxide and 700 g. o-chlorotoluene were azeotropically distilled until the formation of potassium phenoxide was complete. The temperature was reduced to 130° C. and 160.8 g. of a mixture of 15-(62%) and 18- (35%) dichloroanthraquinones were added and the whole stirred first for 3 hours at 130°—5° C. and then for 3 hours more at 150°—5° C. After drowning, steam distilling and isolating the dry product, a yield of 224.8 g. (98.7% of theory) of mixed 1,5- and 1,8-diphenoxyanthraquinones was obtained. Liquid chromatographic analysis showed that the mixture contained 62% 1,5-diphenoxyanthraquinone and 33% 1,8-diphenoxyanthraquinone.

Analysis for residual chlorine: 0.5%.

EXAMPLE 6

1,5-Diphenoxyanthraquinone from 1,5-Dichloroanthraquinone in Xylene

A 1 liter reaction flask equipped with a Dean-Stark phase separator was charged with a mixture of 56.4 g. phenol, 38.2 g. potassium hydroxide, 80.4 g. 1,5-dichloroanthraquinone and 350 g. o-xylene. The whole was stirred at reflux (ca. 130° C.) and in about 5 hours all the reaction-formed water was removed by the phase separator. The reaction was held 8 hours more at reflux (ca. 140° C.) and worked up by drowning into 300 g. of water, steam distilling and recovering the solid product on the filter. After washing neutral and drying, a 97.5 yield (85.7% of theory) of good quality product was obtained.

Analysis for residual chlorine: 0.6%.

What is claimed is:

1. In the manufacture of a phenoxyanthraquinone of the structure

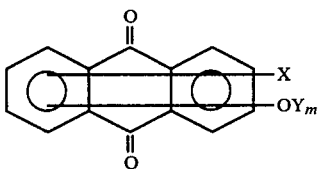

where X is chloro, methyl or hydrogen,

Y is phenyl lower-alkoxyphenyl, or lower alkyl-phenyl at the 1-, 4-, 5- or 8- position, and m is 1 or 2, comprising the step of treating an anthraquinone of the structure

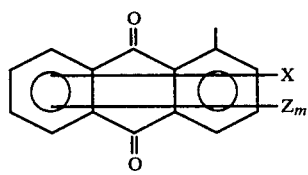

where X is chloro, methyl or hydrogen, selected as above,

Z is chloro or nitro at the position selected for -OY above, provided that Z is nitro when X is chloro, and m is 1 or 2, selected as above, with at least about m equivalents of a phenoxide of structure

YOM where Y is phenyl lower-alkoxyphenyl, or lower-alkylphenyl, selected as above, in a liquid solvent, and M is an alkali metal, the improvement wherein the liquid solvent is a liquid aromatic hydrocarbon or liquid aromatic chlorohydrocarbon, boiling at or above about 90° C. where Z is nitro, or at or above about 120° C. where Z is chloro, used in the absence of excess phenol, water-miscible lower alkanols, and water-miscible polar aprotic solvents.

2. The process of claim 1, wherein X is chloro, Y is phenyl, Z is nitro, m is 1, and M is potassium or sodium.

3. The process of claim 2, where in X is 1-chloro, and Z and YO are attached at the 5- or 8-positions and M is potassium.

4. The process of claim 1, wherein the liquid solvent is selected from the group consisting of chlorobenzene, o-xylene, o-dichlorobenzene and o-chlorotoluene and wherein M is potassium.

5. The process of claim 3, wherein the liquid solvent is o-chlorotoluene.

6. The process of claim 1, wherein X is hydrogen and m is 2.

7. The process of claim 6, wherein both Z groups are chloro or nitro or one Z group is chloro and the other is nitro.

8. The process of claim 6, wherein M is potassium and the liquid solvent is o-chlorotoluene or o-xylene.

9. The process of claim 1 or 6, wherein Y is phenyl, p-tolyl or p-tert-butylphenyl.

10. The process of claim 1, wherein Z is chloro.

11. The process of claim 10, wherein the liquid solvent is selected from the group consisting of chlorobenzene, o-xylene, o-dichlorobenzene and o-chlorotoluene.

12. The process of claim 11, wherein the liquid solvent is o-chlorotoluene.

13. The process of claim 12, wherein M is potassium.

* * * * *